US009724241B2

(12) United States Patent
Ogura et al.

(10) Patent No.: US 9,724,241 B2
(45) Date of Patent: Aug. 8, 2017

(54) SIMPLIFIED HEARING AID

(71) Applicant: Moritaka Ogura, Yokosuka-shi, Kanagawa (JP)

(72) Inventors: Moritaka Ogura, Yokosuka (JP); Morie Ogura, Yokosuka (JP)

(73) Assignee: Moritaka Ogura, Kanagawa (JP)

( * ) Notice: Subject to any disclaimer, the term of this patent is extended or adjusted under 35 U.S.C. 154(b) by 0 days.

(21) Appl. No.: 15/258,678

(22) Filed: Sep. 7, 2016

(65) Prior Publication Data

US 2017/0065457 A1 Mar. 9, 2017

(30) Foreign Application Priority Data

Sep. 8, 2015 (JP) ................................ 2015-176979

(51) Int. Cl.
*A61F 11/00* (2006.01)
*G10K 11/18* (2006.01)
*G10K 11/172* (2006.01)

(52) U.S. Cl.
CPC .......... *A61F 11/008* (2013.01); *G10K 11/172* (2013.01); *G10K 11/18* (2013.01)

(58) Field of Classification Search
CPC ........ A61F 11/008; G10K 11/08; G10K 11/18
USPC .......................... 181/129, 130, 132, 134, 135
See application file for complete search history.

(56) References Cited

U.S. PATENT DOCUMENTS

| | | | | |
|---|---|---|---|---|
| 78,493 A | * | 6/1868 | Stillwell | A61N 1/0526 181/130 |
| 351,398 A | * | 10/1886 | Peck | A61F 2/18 181/134 |
| 419,420 A | * | 1/1890 | Cousins | A61F 2/18 181/134 |
| 534,581 A | * | 2/1895 | Sanford | A61F 2/18 181/134 |
| 565,872 A | * | 8/1896 | Spaulding | H04R 25/652 181/130 |
| 2,097,554 A | * | 11/1937 | Alloway | A61F 11/008 110/101 A |
| 2,641,328 A | * | 6/1953 | Beaudry | A61F 11/008 181/132 |

FOREIGN PATENT DOCUMENTS

| | | |
|---|---|---|
| JP | 64-19589 | 2/1979 |
| JP | 64-52000 | 3/1989 |
| JP | 09-191498 | 7/1997 |

(Continued)

OTHER PUBLICATIONS

International Search Report, Jul. 12, 2016, International Patent Application No. PCT/JP2016/067004 (3 pages).

*Primary Examiner* — Jeremy Luks

(74) *Attorney, Agent, or Firm* — Hamre, Schumann, Mueller & Larson, P.C.

(57) ABSTRACT

A novel hearing aid allowing the user to clearly hear necessary sounds while cutting off noises is provided. The hearing aid includes a cylindrical body to be inserted into the external auditory meatus. The body has an outer surface of such a shape that when the body is inserted into the external auditory meatus, the outer surface substantially sticks firmly to the inner wall of the external auditory meatus. The body has an opening on its insertion end and another opening on its end opposite to the insertion end, both openings communicating without a substantially tapered portion.

10 Claims, 2 Drawing Sheets

(56) References Cited

FOREIGN PATENT DOCUMENTS

| | | |
|---|---|---|
| JP | 10-094615 | 4/1998 |
| JP | 2002-517279 | 6/2002 |
| WO | 2010/040419 | 4/2010 |
| WO | 2011/088887 | 7/2011 |

* cited by examiner

SIMPLIFIED HEARING AID

BACKGROUND OF THE INVENTION

Field of the Invention

The present invention relates to a hearing aid that corrects hearing difficulties caused mainly by aging.

Description of the Related Art

Most of hearing aids known in the art are equipped with a sound amplifier. Such a conventional hearing aid amplifies unnecessary noises together with sounds to hear, posing a problem that the user has difficulty in accurately obtaining essential information during conversations.

Under such circumstances, Japanese Unexamined Patent Application Publication No. 2002-517279 (patent document 1) has proposed a hearing aid requiring no power supply. Patent document 1 has disclosed an earplug that is composed of a first element and a second element, each element having an opening, and that applies an equal pressure to the interior and exterior of the external ear. Patent document 1 states that the earplug allows the user to have a conversation from which noises and unpleasant sounds are cut off.

As described above, the conventional hearing aid poses a problem that it amplifies unnecessary noises to make it difficult for the user, in some cases, to have a smooth conversation.

The earplug described in patent document 1 poses a problem that when the earplug is used, it blocks up most of the external ear and consequently reduces incoming sounds other than noises.

The present invention has been conceived in order to solve the above problems. An object of the present invention is to provide a novel hearing aid that allows the user to clearly hear necessary sounds while cutting off noises.

SUMMARY OF THE INVENTION

The inventors' diligent studies and efforts have led to a finding that a noise cut effect can be achieved without employing a structure blocking up the external ear, such as the earplug described in patent document 1. The inventors have reached a conclusion that using a hearing aid with such a noise cut effect allows the user to clearly hear necessary sounds other than noises.

A hearing aid of the present invention based on the above finding includes a cylindrical body to be inserted into the external auditory meatus. The body has an outer surface of such a shape that when the body is inserted into the external auditory meatus, the outer surface substantially sticks firmly to the inner wall of the external auditory meatus.

The body has an opening on its insertion end and another opening on its end opposite to the insertion end, both openings communicating with each other without a substantially tapered portion.

The hearing aid of the present invention allows the user to clearly hear necessary sounds during a conversation, etc., while cutting off noises.

According to a preferred embodiment of the present invention, the hearing aid is made of a flexible material.

The hearing aid of this embodiment allows its body to stick with high adherence to the inner wall of the external auditory meatus, thus offering a better noise cut effect and improving the clearness of necessary sounds.

According to a preferred embodiment of the present invention, the flexible material is a silicone-based polymer material.

The hearing aid of the present invention made of the silicone-based polymer material aids the user in hearing humane voices. For example, when the user is engaging in a conversation with a person under a noisy environment, the user is able to hear the person's voice even if it is small.

According to a preferred embodiment of the present invention, the body has a substantially uniform thickness.

The substantially uniform thickness of the body improves an effect of providing clear sounds.

According to a preferred embodiment of the present invention, the hearing aid includes a funneled sound collector extending from the opening on the end opposite to the insertion end. A narrow opening of sound corrector and the opening of the end opposite to the insertion end are integrated.

The hearing aid equipped with the sound collector allows the user to clearly hear smaller sounds.

According to a preferred embodiment of the present invention, the sound collector has an outer surface of such a shape that when the body is inserted into the external auditory meatus, the outer surface comes in contact with the inner surface of the cartilaginous portion of external auditory meatus.

The sound collector having such a shape offers an improved sound collection effect.

According to a preferred embodiment of the present invention, when the body is inserted into the external auditory meatus, the edge of the insertion end reaches the vicinity of the osseous portion of external auditory meatus.

This configuration allows the user to utilize the bone condition and clearly hear a sound even if it is small.

The hearing aid of the present invention allows the user to clearly hear necessary sounds while cutting off noises. Preferred embodiments of the present invention allow the user to clearly hear small sounds.

DESCRIPTION OF THE PREFERRED EMBODIMENTS

Embodiments of the present invention will now be described. Obviously, the technical scope of the present invention is not limited to the embodiments.

First Embodiment

Figure 1:
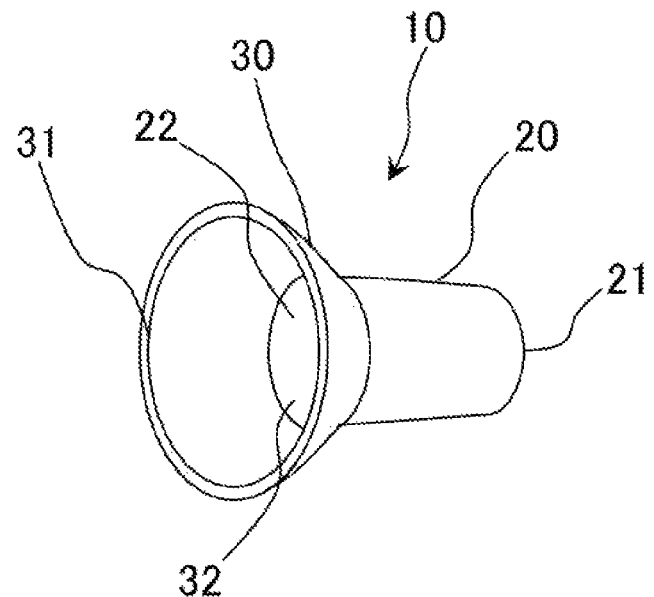
FIG. 1 is a perspective view of a hearing aid according to a first embodiment.
Figure 2:
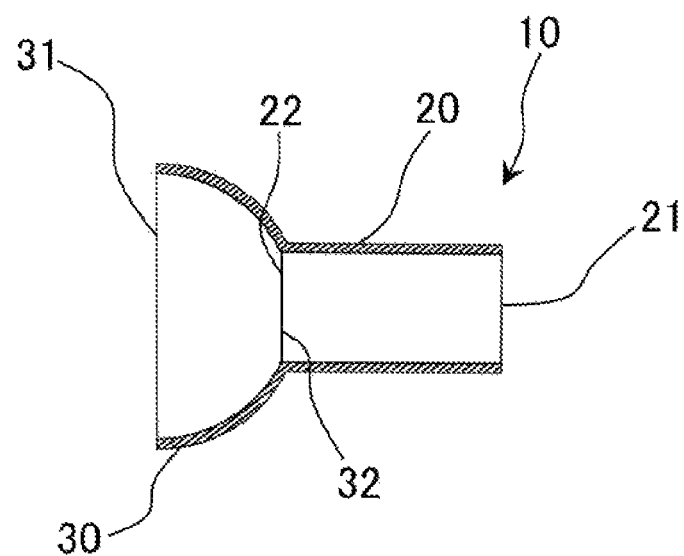
FIG. 2 is a sectional view of the hearing aid of the first embodiment.

A first embodiment will be described, referring to FIGS. 1 to 3.

A hearing aid 10 of the first embodiment includes a cylindrical body 20 and a sound collector 30.

The body 20 has an opening 21 on its insertion end, which is inserted in the external auditory meatus, and an opening 22 on its end opposite to the insertion end. The sound collector 30 is formed integrally with the body 20 such that the sound collector 30 extends from the opening 22 of the body 20. As a result, the opening 22 of the body 20 joins a narrow opening 32 of the sound collector 30 to form an integrated opening (FIGS. 1 and 2).

According to the present invention, the sound collector 30 is provided in a manner described in the first embodiment in which the sound collector 30 has its outer surface stuck firmly to the inner wall of an external auditory meatus 41 to increase an area where the sound collector 30 sticks firmly to the external auditory meatus 41. This enhances a sound collection effect, allowing the user to clearly hear small sounds. The body 20 and the sound collector 30 are made of either the same material or different materials. It is preferable that the body 20 and the sound collector 30 be made from the same material into an integral structure.

Materials making up the body 20 and the sound collector 30 of the hearing aid 10 according to the first embodiment should preferably be flexible materials, which include, for example, synthetic resins, such as polyethylene, polypropylene, polyester, and polyurethane, and synthetic rubbers or natural rubbers, such as silicone-based polymer and urethane rubbers.

Using such flexible materials improves the adherence of the body 20 to the inner wall of the external auditory meatus 41, thereby enhances a noise cut effect and improves the clearness of necessary sounds.

According to a more preferred embodiment of the present invention, a silicone-based polymer material is adopted as the raw material for the hearing aid 10.

The silicone-based polymer material is used as the raw material for a pseudo respiratory tract, a pseudo vocal cord, a pseudo tongue, and pseudo lips in an artificial vocal apparatus because of the polymer material's feature that its resonance frequency tends to corresponds to the frequency of human voice. The hearing aid 10 made from the silicone-based polymer material resonates not with noise but with human voice, and vibrates, thereby transmits a sound to the inner ear directly or through bone conduction. The hearing aid 10 made from the silicone-based polymer material, therefore, allows the user to hear a voice from a person with whom the user is having a conversation under a noisy environment, even if the voice is small.

Figure 3:
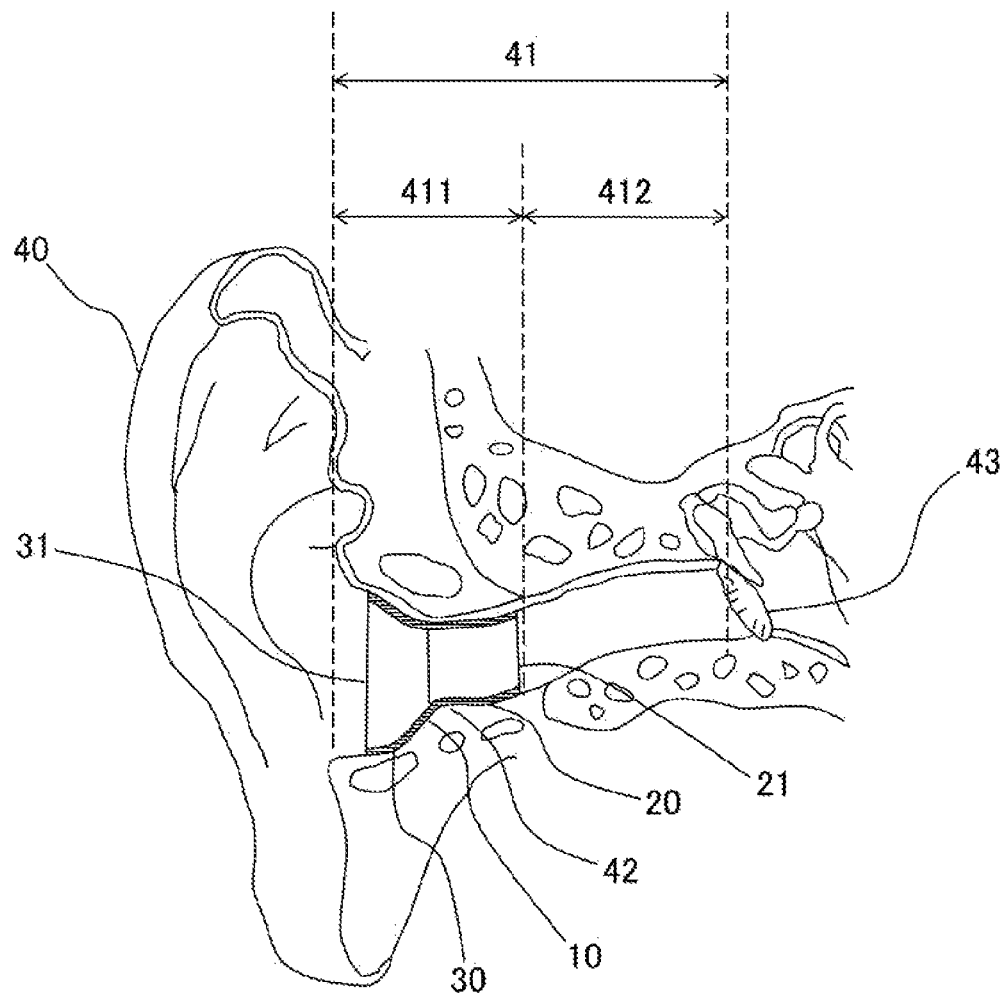
FIG. 3 is a sectional view of the hearing aid of the first embodiment that is inserted into the external auditory meatus.

The body 20 should have a shape such that when the body 20 is inserted into the external auditory meatus 41, the body 20 substantially sticks firmly to the inner wall of the external auditory meatus 41 (FIG. 3). The body 20 does not have to take such a shape before it is inserted into the external auditory meatus 41 (FIGS. 1 and 2).

In the hearing aid 10, the opening 21 and the opening 22 communicate with each other without a substantially tapered portion. The phrase "substantially tapered" does not refer to a case where the openings 21 and 22 and the inner space of the body 20 are tapered because of the shape of the external auditory meatus.

The body 20 should preferably have a length such that when the body 20 is inserted deep enough to locate the edge of the end opposite to the insertion end in the vicinity of a ceruminous gland 42, the edge of the insertion end reaches the vicinity of the osseous portion of external auditory meatus 412 (FIG. 3).

The body having such a length is allowed to utilize bone conduction through which the user is able to hear smaller sounds.

The sound collector 30, whose size is not limited specifically, is given a size such that its wide opening 31 is located near the entrance of a cartilaginous portion of external auditory meatus 411 (FIG. 3). The sound collector 30 should preferably be given a shape such that the outer periphery of the sound collector 30 is in contact with the inner wall of the cartilaginous portion of external auditory meatus 411 (FIG. 3). The sound collector 30 of such a shape increases an area where the outer surface of the hearing aid 10 sticks firmly to the inner surface of the external auditory meatus 41, as shown in FIG. 3, thus improving a sound collection effect by the hearing aid 10.

Each of the body 20 and the sound collector 30, whose thicknesses are not limited specifically, should preferably be 1 to 2 mm in thickness. Giving the body 20 and sound collector 30 such a thickness ensures the sufficient diameter of the inner space of the body 20, which spares the user a choking or oppressive feeling.

The present invention is applicable to a hearing aid that corrects hearing difficulties caused by aging.

What is claimed is:

1. A hearing aid that is inserted into an external auditory meatus when used, the hearing aid consisting of:
   a cylindrical body; and
   a funneled sound collector connected to one end of the body, wherein
   the body and the sound collector communicate with each other without a substantially tapered portion and are formed to have a substantially uniform thin wall extending from the body to the sound collector, and
   when the body and the sound collector are inserted into the external auditory meatus with the body being inserted first, outer surfaces of the body and the sound collector substantially stick firmly to an inner wall of the external auditory meatus.

2. The hearing aid according to claim 1, wherein
   the body and the sound collector are made of a flexible material.

3. The hearing aid according to claim 2, wherein
   the flexible material is a silicone-based polymer material.

4. The hearing aid according to claim 1, wherein
   when the hearing aid is inserted into the external auditory meatus, an outer surface of the sound collector is in contact with an inner wall of a cartilaginous portion of external auditory meatus.

5. The hearing aid according to claim 1, wherein
   when the hearing aid is inserted into the external auditory meatus, an edge of an insertion end of the body is located in vicinity of an osseous portion of external auditory meatus.

6. The hearing aid according to claim 1, wherein the body has an insertion end and an opposite end that is connected to the sound collector, and the body has a constant diameter from the insertion end to the opposite end.

7. The hearing aid according to claim 6, wherein the insertion end is open and the opposite end is open.

8. The hearing aid according to claim 1, wherein the sound collector has an exterior surface that is convex outwardly an entire distance from a wide opening to where the sound collector is connected to the body.

9. The hearing aid according to claim 1, wherein the body and the sound collector have a constant thickness from one end of the hearing aid to a second end thereof.

10. The hearing aid according to claim 1, wherein the body and the sound collector consist of a single flexible material.

* * * * *